United States Patent
Wu et al.

(10) Patent No.: US 12,378,538 B2
(45) Date of Patent: *Aug. 5, 2025

(54) PHYTASE MUTANT

(71) Applicant: QINGDAO VLAND BIOTECH GROUP CO., LTD, Shandong (CN)

(72) Inventors: Xiuxiu Wu, Shandong (CN); Yijun Huang, Shandong (CN); Yang Liu, Shandong (CN); Xia Zhang, Shandong (CN); Sida Cheng, Shandong (CN)

(73) Assignee: QINGDAO VLAND BIOTECH GROUP CO., LTD, Shandong (CN)

( * ) Notice: Subject to any disclaimer, the term of this patent is extended or adjusted under 35 U.S.C. 154(b) by 874 days.

This patent is subject to a terminal disclaimer.

(21) Appl. No.: 17/431,185

(22) PCT Filed: Feb. 11, 2020

(86) PCT No.: PCT/CN2020/074735
§ 371 (c)(1),
(2) Date: Aug. 16, 2021

(87) PCT Pub. No.: WO2020/168943
PCT Pub. Date: Aug. 27, 2020

(65) Prior Publication Data
US 2022/0154154 A1 May 19, 2022

(30) Foreign Application Priority Data

Feb. 18, 2019 (CN) .......................... 201910119308.0

(51) Int. Cl.
*C12N 9/16* (2006.01)
*C12N 15/81* (2006.01)

(52) U.S. Cl.
CPC ............. *C12N 9/16* (2013.01); *C12N 15/815* (2013.01); *C12Y 301/03* (2013.01)

(58) Field of Classification Search
CPC ....... C12N 15/815; C12N 9/16; C12Y 301/03
See application file for complete search history.

(56) References Cited

U.S. PATENT DOCUMENTS

| | | | |
|---|---|---|---|
| 9,194,010 B2 * | 11/2015 | Guo | .......................... C12N 9/16 |
| 2020/0362356 A1 | 11/2020 | Wu et al. | |
| 2023/0242890 A1 * | 8/2023 | Wu | ................ C12Y 301/03008 435/196 |

FOREIGN PATENT DOCUMENTS

| | | | |
|---|---|---|---|
| CN | 102002487 A | | 4/2011 |
| CN | 103205443 A | * | 7/2013 |
| EP | 3222714 A1 | | 9/2017 |
| WO | WO-2010135588 A2 | * | 11/2010 ......... A01K 67/0275 |

OTHER PUBLICATIONS

GenCore Alignment Results (Year: 2024).*
CN103205443, WIPO Machine Translation, pp. 1-6 (Year: 2013).*
CN103205443, Espacenet Machine Translation, pp. 1-6. (Year: 2013).*
GenCore Sequence Alignment No. 1 (Instant Seq ID No. 1 aligned with Liang's Seq ID No. 2 ) Results pp. 1-2. (Year: 2024).*
GenCore Sequuence Alignment No. 3 (Instant Seq ID No. 1 aligned with Weiner's Variant 77) Results pp. 1-2. (Year: 2024).*
GenCore Sequence Alignment Results, Guo et al., Seq ID No. 4 vs. Instant Seq ID No. 1, pp. 1-2. (Year: 2025).*
International Search Report for PCT/CN2020/074735 mailed May 14, 2020, ISA/CN.
Wang Qian et al., Improving the thermostability of *Escherichia coli* phytase AppA multipoint mutation, High Technology Letters, vol. 24, Dec. 31, 2014.
Yao Mz et al., Improving the thermostability of *Escherichia coli* phytase, appA, by enhancement of glycosylation, Biotechnology Letters, vol. 35, Oct. 31, 2013.
Database UniProt [Online] Jul. 5, 2017 (Jul. 5, 2017), "SubName: Full=Periplasmic AppA protein {ECO:0000313| EMBL:OSL 14263. 1};", retrieved from EBI accession No. UNIPROT:A0A1X3JKJ5, Database accession No. A0A1X3JKJ5.
Database Geneseq [Online] Jan. 16, 2014 (Jan. 16, 2014), "*Escherichia coli* phytase (Appa-M2) mutant Q258N/Q349N, SEQ ID 2.", retrieved from EBI accession No. GSP:BAY29388 Database accession No. BAY29388.
Li Jiadi et al: "Evolution of *E. coli* Phytase for Increased Thermostability Guided by Rational Parameters", Journal of Microbiology and Biotechnology, vol. 29, No. 3, Mar. 28, 2019 (Mar. 28, 2019), pp. 419-428, XP055975773.
European search report issued on Nov. 29, 2022 for EP20759529.9.

* cited by examiner

Primary Examiner — Lianko G Garyu
Assistant Examiner — Claudia Espinosa
(74) Attorney, Agent, or Firm — Yue (Robert) Xu; Apex Attorneys at Law, LLP

(57) ABSTRACT

The present invention relates to the technical field of biology, in particular to a phytase mutant, a preparation method therefor and an application thereof, a DNA molecule encoding the phytase mutant, a vector, and a host cell. The mutant provided by the present invention contains the substituent of an amino acid at at least one position selected from the following group: 36, 69, 89, 91, 111, 202, 213, 225, 238, 243, 253, 258, and 266. The heat resistance of the mutant is significantly improved, thereby facilitating the wide application of the phytase in feed.

8 Claims, No Drawings
Specification includes a Sequence Listing.

```
                            SEQUENCE LISTING

<160> NUMBER OF SEQ ID NOS: 20

<210> SEQ ID NO 1
<211> LENGTH: 410
<212> TYPE: PRT
<213> ORGANISM: Escherichia coli

<400> SEQUENCE: 1

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Trp Leu Thr
        35                  40                  45

Pro Arg Gly Gly Glu Leu Ile Ala Tyr Leu Gly His Tyr Gln Arg Gln
    50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Asn Ala Asn Val Thr Asp Ala Ile
    130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Gln Trp Ile Gln Val Ser Leu
            340                 345                 350
```

```
Val Phe Gln Thr Leu Gln Gln Met Arg Asp Lys Thr Pro Leu Ser Leu
            355                 360                 365

Asn Thr Pro Pro Gly Glu Val Lys Leu Thr Leu Ala Gly Cys Glu Glu
        370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 2
<211> LENGTH: 1233
<212> TYPE: DNA
<213> ORGANISM: Escherichia coli

<400> SEQUENCE: 2
cagagtgagc cggagctgaa gctggaaagt gtggtgattg tcagtcgtca tggtgtgcgt      60
gctccaacca aggccacgca actgatgcag gatgtcaccc cagacgcatg gccaacctgg     120
ccggtaaaac tgggttggct gacaccgcgc ggtggtgagc taatcgccta tctcggacat     180
taccaacgcc agcgtctggt agccgacgga ttgctggcga aaaagggctg cccgcagtct     240
ggtcaggtcg cgattattgc tgatgtcgac gagcgtaccc gtaaaacagg cgaagccttc     300
gccgccgggc tggcacctga ctgtgcaata accgtacata cccaggcaga tacgtccagt     360
cccgatccgt tatttaatcc tctaaaaact ggcgtttgcc aactggataa cgcgaacgtg     420
actgacgcga tcctcagcag ggcaggaggg tcaattgctg actttaccgg catcggcaa     480 acggcgtttc gcgaactgga cgggtgctt aattttccgc aatcaaactt gtgccttaaa     540
cgtgagaaac aggacgaaag ctgttcatta acgcaggcat taccatcgga actcaaggtg     600
agcgccgaca atgtctcatt aaccggtgcg gtaagcctcg catcaatgct gacggagata     660
tttctcctgc aacaagcaca gggaatgccg gagccggggt ggggaaggat caccgattca     720
caccagtgga acaccttgct aagtttgcat aacgcgcaat tttatttgct acaacgcacg     780
ccagaggttg cccgcagccg cgccaccccg ttattagatt tgatcaagac agcgttgacg     840
ccccatccac cgcaaaaaca ggcgtatggt gtgacattac ccacttcagt gctgtttatc     900
gccggacacg atactaatct ggcaaatctc ggcggcgcac tggagctcaa ctggacgctt     960
cccggtcagc cggataacac gccgccaggt ggtgaactgg tgtttgaacg ctggcgtcgg    1020
ctaagcgata acagccagtg gattcaggtt tcgctggtct tccagacttt acagcagatg    1080
cgtgataaaa cgccgctgtc attaaatacg ccgcccggag aggtgaaact gaccctggca    1140
ggatgtgaag agcgaaatgc gcagggcatg tgttcgttgg caggttttac gcaaatcgtg    1200
aatgaagcac gcataccggc gtgcagtttg taa                                 1233

<210> SEQ ID NO 3
<211> LENGTH: 32
<212> TYPE: DNA
<213> ORGANISM: Artificial Sequence
<220> FEATURE:
<223> OTHER INFORMATION: Synthesized Primer

<400> SEQUENCE: 3
ggcgaattcc agtcagaacc agagttgaag tt                                    32

<210> SEQ ID NO 4
<211> LENGTH: 32
<212> TYPE: DNA
<213> ORGANISM: Artificial Sequence
```

<220> FEATURE:
<223> OTHER INFORMATION: Synthesized Primer

<400> SEQUENCE: 4
atagcggccg cttacaagga acaagcaggg at                          32

<210> SEQ ID NO 5
<211> LENGTH: 410
<212> TYPE: PRT
<213> ORGANISM: Artificial Sequence
<220> FEATURE:
<223> OTHER INFORMATION: Synthesized Amino acid sequence of M1

<400> SEQUENCE: 5

```
Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Trp Leu Thr
        35                  40                  45

Pro Arg Gly Gly Glu Leu Ile Ala Tyr Leu Gly His Tyr Gln Arg Gln
    50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Asn Ala Asn Val Thr Asp Ala Ile
    130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Glu Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Gly Gly Glu Leu Val Phe Glu
                325                 330                 335
```

Arg Trp Arg Arg Leu Ser Asp Asn Ser Gln Trp Ile Gln Val Ser Leu
                340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Ala Gly Cys Glu Glu
370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 6
<211> LENGTH: 1230
<212> TYPE: DNA
<213> ORGANISM: Artificial Sequence
<220> FEATURE:
<223> OTHER INFORMATION: Synthesized Nucleotide sequence encoding M1

<400> SEQUENCE: 6
caatccgagc cagagttgaa gttggagtcc gttgttatcg tttccagaca cggtgttaga      60
gccccaacta aggctactca attgatgcag gatgttactc cagacgcttg gccaacttgg     120
cctgtaaaac ttggttggtt gactccaaga ggtggtgagt tgattgctta cttgggtcac     180
taccagagac agagattggt tgctgatggt tgtgttggcta agaagggttg tccacaatcc    240
ggtcaggttg ctattattgc tgacgttgac gagagaacca gaaagactgg tgaggctttt    300
gctgctggat tggctccaga ttgtgctatc actgttcaca ctcaagccga cacttcatcc    360
ccagatcctt tgttcaaccc acttaagacc ggtgtttgcc agttggacaa cgctaacgtt    420
actgacgcta tcttgtctag agccggtggt tccattgctg atttcactgg tcatagacag    480
accgccttca gagaattgga gagagtcttg aacttccac agtccaacct gtgtttgaag    540
agagagaagc aagacgagtc ctgctctttg actcaggctt tgccatctga gttgaaggtt    600
tccgctgaca acgtttcctt gactggtgct gttttctttgg cctccatgct gaccgagatt    660
ttcttgttgc agcaagctca aggtatgcca gaaccaggtt ggggtagaat tactgactct    720
caccagtgga acaccttgtt gtccttgcac aacgctcagt tctacttgct ggagagaact    780
ccagaagttg ctagatccag agctacccct tgttggact tgattaagac cgcttttgacc    840 ccacatccac cacaaaagca ggcttacggt gttactttgc caacctccgt tttgttcatt    900
gctggtcacg acactaacct ggctaaccttt ggtggtgctt tggagttgaa ctggactttg    960
ccaggtcaac cagataacac tccaccaggt ggtgaattgg ttttcgagag atggcgtaga   1020
ttgtccgaca actcccaatg gattcaggtt tccttggtgt tccaaacctt gcagcagatg   1080
agagacaaga ccccattgtc cttgaatact cctccaggtg aggttaagtt gaccttggct   1140
ggttgtgagg aaagaaacgc tcagggtatg tgttccttgg ccggtttcac tcaaattgtc   1200
aacgaggcta gaatccccgc ttgttcctta                                      1230

<210> SEQ ID NO 7
<211> LENGTH: 410
<212> TYPE: PRT
<213> ORGANISM: Artificial Sequence
<220> FEATURE:
<223> OTHER INFORMATION: Synthesized Amino acid sequence of M2

<400> SEQUENCE: 7

Gln Ser Glu Pro Glu Leu Lys Leu Glu Ser Val Val Ile Val Ser Arg

```
  1               5                    10                   15
His Gly Val Arg Ala Pro Thr Lys Ala Thr Gln Leu Met Gln Asp Val
                20                  25                  30

Thr Pro Asp Ala Trp Pro Thr Trp Pro Val Lys Leu Gly Trp Leu Thr
                35                  40                  45

Pro Arg Gly Gly Glu Leu Ile Ala Tyr Leu Gly His Tyr Gln Arg Gln
                50                  55                  60

Arg Leu Val Ala Asp Gly Leu Leu Ala Lys Lys Gly Cys Pro Gln Ser
 65                 70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
               100                 105                 110

His Thr Gln Ala Asp Thr Ser Ser Pro Asp Pro Leu Phe Asn Pro Leu
               115                 120                 125

Lys Thr Gly Val Cys Gln Leu Asp Asn Ala Asn Val Thr Asp Ala Ile
130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
                180                 185                 190

Ala Leu Pro Ser Glu Leu Lys Val Ser Ala Asp Asn Val Ser Leu Thr
                195                 200                 205

Gly Ala Val Ser Leu Ala Ser Met Leu Thr Glu Ile Phe Leu Leu Gln
210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Pro Arg Ala Thr Pro Leu Leu
                260                 265                 270

Asp Leu Ile Lys Thr Ala Leu Thr Pro His Pro Pro Gln Lys Gln Ala
                275                 280                 285

Tyr Gly Val Thr Leu Pro Thr Ser Val Leu Phe Ile Ala Gly His Asp
                290                 295                 300

Thr Asn Leu Ala Asn Leu Gly Ala Leu Glu Leu Asn Trp Thr Leu
305                 310                 315                 320

Pro Gly Gln Pro Asp Asn Thr Pro Pro Gly Gly Leu Val Phe Glu
                325                 330                 335

Arg Trp Arg Arg Leu Ser Asp Asn Ser Gln Trp Ile Gln Val Ser Leu
                340                 345                 350

Val Phe Gln Thr Leu Gln Gln Met Arg Asp Lys Thr Pro Leu Ser Leu
                355                 360                 365

Asn Thr Pro Pro Gly Glu Val Lys Leu Thr Leu Ala Gly Cys Glu Glu
                370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 8
```

<211> LENGTH: 1230
<212> TYPE: DNA
<213> ORGANISM: Artificial Sequence
<220> FEATURE:
<223> OTHER INFORMATION: Synthesized Nucleotide sequence encoding M2

<400> SEQUENCE: 8

```
caatccgagc cagagttgaa gttggagtcc gttgttatcg tttccagaca cggtgttaga      60
gccccaacta aggctactca attgatgcag gatgttactc cagacgcttg gccaacttgg     120
cctgtaaaac ttggttggtt gactccaaga ggtggtgagt tgattgctta cttgggtcac     180
taccagagac agagattggt tgctgatggt ttgttggcta agaagggttg tccacaatcc     240
ggtcaggttg ctattattgc tgacgttgac gagagaacca gaaagactgg tgaggctttt     300
gctgctggat tggctccaga ttgtgctatc actgttcaca ctcaagccga cacttcatcc     360
ccagatcctt tgttcaaccc acttaagacc ggtgtttgcc agttggacaa cgctaacgtt     420
actgacgcta tcttgtctag gccggtggt tccattgctg atttcactgg tcatagacag      480
accgccttca gagaattgga gagagtcttg aacttcccac agtccaacct gtgtttgaag     540
agagagaagc aagacgagtc ctgctctttg actcaggctt tgccatctga gttgaaggtt     600
tccgctgaca acgtttcctt gactggtgct gtttctttgg cctccatgct gaccgagatt     660
ttcttgttgc agcaagctca aggtatgcca gaaccaggtt ggggtagaat tactgactct     720
caccagtgga acaccttgtt gtccttgcac aacgctcagt tctacttgct gcagagaact     780
ccagaagttg ctagaccaag agctaccccct tgttggact tgattaagac cgctttgacc    840
ccacatccac cacaaaagca ggcttacggt gttactttgc caacctccgt tttgttcatt     900
gctggtcacg acactaacct ggctaacctt ggtggtgctt tggagttgaa ctggactttg     960
ccaggtcaac cagataacac tccaccaggt ggtgaattgg ttttcgagag atggcgtaga    1020
ttgtccgaca actcccaatg gattcaggtt tccttggtgt tccaaacctt gcagcagatg    1080
agagacaaga ccccattgtc cttgaatact cctccaggtg aggttaagtt gaccttggct    1140
ggttgtgagg aaagaaacgc tcagggtatg tgttccttgg ccggtttcac tcaaattgtc    1200
aacgaggcta gaatccccgc ttgttcctta                                      1230
```

<210> SEQ ID NO 9
<211> LENGTH: 410
<212> TYPE: PRT
<213> ORGANISM: Artificial Sequence
<220> FEATURE:
<223> OTHER INFORMATION: Synthesized Amino acid sequence of M3

<400> SEQUENCE: 9

```
Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Trp Leu Thr
        35                  40                  45

Pro Arg Gly Gly Glu Leu Ile Ala Tyr Leu Gly His Tyr Gln Arg Gln
    50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
```

```
            100                 105                 110
His Thr Gln Ala Asp Thr Ser Ser Pro Asp Pro Leu Phe Asn Pro Leu
            115                 120                 125

Lys Thr Gly Val Cys Gln Leu Asp Asn Ala Asn Val Thr Asp Ala Ile
130                 135                 140

Leu Ser Arg Ala Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                    165                 170                 175

Leu Cys Leu Lys Arg Glu Lys Gln Asp Glu Ser Cys Ser Leu Thr Gln
                180                 185                 190

Ala Leu Pro Ser Glu Leu Lys Val Ser Ala Asp Asn Val Ser Leu Thr
            195                 200                 205

Gly Ala Val Ser Leu Ala Ser Met Leu Thr Glu Ile Phe Leu Leu Gln
            210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                    245                 250                 255

Leu Glu Arg Thr Pro Glu Val Ala Arg Pro Arg Ala Thr Pro Leu Leu
                260                 265                 270

Asp Leu Ile Lys Thr Ala Leu Thr Pro His Pro Pro Gln Lys Gln Ala
            275                 280                 285

Tyr Gly Val Thr Leu Pro Thr Ser Val Leu Phe Ile Ala Gly His Asp
            290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                    325                 330                 335

Arg Trp Arg Arg Leu Ser Asp Asn Ser Gln Trp Ile Gly Val Ser Leu
                340                 345                 350

Val Phe Gln Thr Leu Gln Gln Met Arg Asp Lys Thr Pro Leu Ser Leu
            355                 360                 365

Asn Thr Pro Pro Gly Glu Val Lys Leu Thr Leu Ala Gly Cys Glu Glu
            370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                    405                 410

<210> SEQ ID NO 10
<211> LENGTH: 1230
<212> TYPE: DNA
<213> ORGANISM: Artificial Sequence
<220> FEATURE:
<223> OTHER INFORMATION: Synthesized Nucleotide sequence encoding M3

<400> SEQUENCE: 10
caatccgagc cagagttgaa gttggagtcc gttgttatcg tttccagaca cggtgttaga      60
gccccaacta aggctactca attgatgcag gatgttactc cagacgcttg gccaacttgg     120
cctgtaaaac ttggttggtt gactccaaga ggtggtgagt gattgcttta cttgggtcac     180
taccagagac agagattggt tgctgatggt ttgttggcta agaagggttg tccacaatcc     240
ggtcaggttg ctattattgc tgacgttgac gagagaacca gaaagactgg tgaggctttt     300
```

```
gctgctggat tggctccaga ttgtgctatc actgttcaca ctcaagccga cacttcatcc    360
ccagatcctt tgttcaaccc acttaagacc ggtgtttgcc agttggacaa cgctaacgtt    420
actgacgcta tcttgtctag agccggtggt tccattgctg atttcactgg tcatagacag    480
accgccttca gagaattgga gagagtcttg aacttcccac agtccaacct gtgtttgaag    540
agagagaagc aagacgagtc ctgctctttg actcaggctt gccatctga gttgaaggtt    600
tccgctgaca acgtttcctt gactggtgct gtttctttgg cctccatgct gaccgagatt    660
ttcttgttgc agcaagctca aggtatgcca gaaccaggtt ggggtagaat tactgactct    720
caccagtgga acaccttgtt gtccttgcac aacgctcagt tctacttgct ggagagaact    780
ccagaagttg ctagaccaag agctaccct tgttggact tgattaagac cgctttgacc    840
ccacatccac cacaaaagca ggcttacggt gttactttgc aacctccgt tttgttcatt    900
gctggtcacg acactaacct ggctaacctt ggtggtgctt tggagttgaa ctggactttg    960
ccaggtcaac cagataacac tccaccaggt ggtgaattgg ttttcgagag atggcgtaga    1020
ttgtccgaca actcccaatg gattcaggtt tccttggtgt tccaaacctt gcagcagatg    1080
agagacaaga ccccattgtc cttgaatact cctccaggtg aggttaagtt gaccttggct    1140
ggttgtgagg aaagaaacgc tcagggtatg tgttccttgg ccggtttcac tcaaattgtc    1200
aacgaggcta gaatccccgc ttgttcctta                                      1230
```

<210> SEQ ID NO 11  
<211> LENGTH: 410  
<212> TYPE: PRT  
<213> ORGANISM: Artificial Sequence  
<220> FEATURE:  
<223> OTHER INFORMATION: Synthesized Amino acid sequence of M4

<400> SEQUENCE: 11

```
Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
                20                  25                  30

Thr Pro Asp Ala Trp Pro Thr Trp Pro Val Lys Leu Gly Glu Leu Thr
        35                  40                  45

Pro Arg Gly Gly Glu Leu Ile Ala Tyr Leu Gly His Tyr Trp Arg Gln
    50                  55                  60

Arg Leu Val Ala Asp Glu Leu Leu Pro Lys Cys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
                100                 105                 110

His His Gln Ala Asp Thr Ser Ser Pro Asp Pro Leu Phe Asn Pro Leu
        115                 120                 125

Lys Thr Gly Val Cys Gln Leu Asp Val Ala Asn Val Thr Arg Ala Ile
    130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
                180                 185                 190

Ala Leu Pro Ser Glu Leu Lys Val Ser Ala Asp Asn Val Ser Leu Thr
```

195                 200                 205
Gly Ala Val Ser Leu Ala Ser Met Leu Thr Glu Ile Phe Leu Leu Gln
    210                 215                 220
Gln Ala Gln Gly Met Pro Glu Pro Gly Trp Gly Arg Ile Thr Asp Ser
225                 230                 235                 240
His Gln Trp Asn Thr Leu Leu Ser Leu His Asn Ala Gln Phe Asp Leu
                245                 250                 255
Leu Glu Arg Thr Pro Glu Val Ala Arg Ser Arg Ala Thr Pro Leu Leu
            260                 265                 270
Asp Leu Ile Lys Thr Ala Leu Thr Pro His Pro Pro Gln Lys Gln Ala
        275                 280                 285
Tyr Gly Val Thr Leu Pro Thr Ser Val Leu Phe Ile Ala Gly His Asp
    290                 295                 300
Thr Asn Leu Ala Asn Leu Gly Gly Ala Leu Glu Leu Asn Trp Thr Leu
305                 310                 315                 320
Pro Gly Gln Pro Asp Asn Thr Pro Pro Gly Gly Glu Leu Val Phe Glu
                325                 330                 335
Arg Trp Arg Arg Leu Ser Asp Asn Ser Gln Trp Ile Gln Val Ser Leu
            340                 345                 350
Val Phe Gln Thr Leu Gln Gln Met Arg Asp Lys Thr Pro Leu Ser Leu
        355                 360                 365
Asn Thr Pro Pro Gly Glu Val Lys Leu Thr Leu Ala Gly Cys Glu Glu
    370                 375                 380
Arg Asn Ala Gln Gly Met Cys Ser Leu Ala Gly Phe Thr Gln Ile Val
385                 390                 395                 400
Asn Glu Ala Arg Ile Pro Ala Cys Ser Leu
                405                 410

<210> SEQ ID NO 12
<211> LENGTH: 1233
<212> TYPE: DNA
<213> ORGANISM: Artificial Sequence
<220> FEATURE:
<223> OTHER INFORMATION: Synthesized Nucleotide sequence encoding M4

<400> SEQUENCE: 12
cagtcagaac cagagttgaa gttggagtca gtcgtcatcg ttagtagaca tggagttaga      60
gccccctacaa aggctaccca gcttatgcaa gatgttaccc cagacgcttg gccaacttgg    120
cctgtcaagt tgggagaact tactcctaga ggtggagagt tgattgccta ccttggtcat    180
tattggagac aaagattggt tgcagatgaa ttgcttccaa agtgtggttg ccctcaatct    240
ggacaggttg caattatcgc tgatgttgat gaaagaacta gaaaaacagg agaggctttt    300
gctgccggat tggccccaga ttgtgcaatc actgttcatc accaagccga tacatcttcc    360
ccagaccctt tgttcaaccc tcttaagaca ggagtctgtc agttggatgt tgccaatgtc    420
accagagcaa ttttggaaag agctggtgga agtatcgccg actttactgg tcactaccaa    480
acagctttca gagaattgga gagagttctt aactttccac agtccaattt gtgtcttaag    540
agagaaaagc aagatgagtc atgcagtttg actcaggctc ttccttctga gttgaaagtt    600
tccgccgaca acgtctcatt gaccggagct gtttctcttg cctccatgtt gactgaaatt    660
ttccttgcttc aacaggctca gggtatgcca gagcctggtt ggggaagaat caccgatagt    720
catcagtgga cactttgct ttcttttgcac aatgctcaat cgacttgct tgagagaact    780
ccagaagttg caagatccag agctacacct ttgcttgatc ttattaagac cgcattgact    840

```
ccacatccac ctcaaaaaca ggcttatgga gttacattgc ctacctctgt cttgttcatc    900
gctggtcacg acactaactt ggcaaatctt ggtggagctt tggagcttaa ctggacattg    960
ccaggtcaac ctgataatac cccacctggt ggagaattgg ttttgagag atggagaaga    1020 ttgtcagaca atagtcaatg gattcaggtt ccttggtct tccaaacttt gcaacagatg    1080
agagataaga caccattgtc acttaacacc ccacctggtg aagtcaaatt gacacttgcc    1140
ggatgtgaag agaaaatgc acaaggaatg tgcagtcttg ctggtttcac ccaaatcgtc    1200
aatgaggcta gaatccctgc ttgttccttg taa                                 1233
```

<210> SEQ ID NO 13
<211> LENGTH: 410
<212> TYPE: PRT
<213> ORGANISM: Artificial Sequence
<220> FEATURE:
<223> OTHER INFORMATION: Synthesized Amino acid sequence of M5

<400> SEQUENCE: 13

```
Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Glu Leu Thr
        35                  40                  45

Pro Arg Gly Gly Glu Leu Ile Ala Tyr Leu Gly His Tyr Trp Arg Gln
    50                  55                  60

Arg Leu Val Ala Asp Glu Leu Leu Pro Lys Cys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His His Gln Ala Asp Thr Ser Ser Pro Asp Pro Leu Phe Asn Pro Leu
        115                 120                 125

Lys Thr Gly Val Cys Gln Leu Asp Val Ala Asn Val Thr Arg Ala Ile
    130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Pro Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
```

```
                    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
                340                 345                 350

Val Phe Gln Thr Leu Gln Gln Met Arg Asp Lys Thr Pro Leu Ser Leu
            355                 360                 365

Asn Thr Pro Pro Gly Glu Val Lys Leu Thr Leu Ala Gly Cys Glu Glu
        370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 14
<211> LENGTH: 1233
<212> TYPE: DNA
<213> ORGANISM: Artificial Sequence
<220> FEATURE:
<223> OTHER INFORMATION: Synthesized Nucleotide sequence encoding M5

<400> SEQUENCE: 14
cagtcagaac cagagttgaa gttggagtca gtcgtcatcg ttagtagaca tggagttaga      60 gccctacaa aggctaccca gcttatgcaa gatgttaccc cagacgcttg gccaacttgg     120
cctgtcaagt tgggagaact tactcctaga ggtggagagt tgattgccta ccttggtcat     180
tattggagac aaagattggt tgcagatgaa ttgcttccaa agtgtggttg ccctcaatct     240
ggacaggttg caattatcgc tgatgttgat gaaagaacta gaaaaacagg agaggctttt     300
gctgccggat tggccccaga ttgtgcaatc actgttcatc accaagccga tacatcttcc     360
ccagaccctt tgttcaaccc tcttaagaca ggagtctgtc agttggatgt tgccaatgtc     420
accagagcaa ttttggaaag agctggtgga agtatcgccg actttactgg tcactaccaa     480
acagctttca gagaattgga gagagttctt aactttccac agtccaattt tgtgtcttaag    540 agagaaaagc aagatgagtc atgcagtttg actcaggctc ttccttctga gttgaaagtt    600
tccgccgaca acgtctcatt gaccggagct gtttctcttg cctccatgtt gactgaaatt    660
ttcttgcttc aacaggctca gggtatgcca gagcctggtt ggggaagaat caccgatagt    720
catcagtgga cactttgct ttcttttgcac aatgctcaat tcgacttgct tcagagaact    780
ccagaagttg caagaccaag agctacacct ttgcttgatc ttattaagac cgcattgact    840
ccacatccac ctcaaaaaca ggcttatgga gttacattgc ctacctctgt cttgttcatc    900
gctggtcacg acactaactt ggcaaatctt ggtggagctt tggagcttaa ctggacattg    960
ccaggtcaac tgataatac cccacctggt ggagaattgg ttttttgagag atggagaaga   1020 ttgtcagaca atagtcaatg gattcaggtt tccttggtct tccaaacttt gcaacagatg   1080
agagataaga caccattgtc acttaacacc ccacctggtg aagtcaaatt gacacttgcc   1140
ggatgtgaag agagaaatgc acaaggaatg tgcagtcttg ctggttttcac ccaaatcgtc   1200 aatgaggcta gaatccctgc ttgttccttg taa                                 1233

<210> SEQ ID NO 15
<211> LENGTH: 410
<212> TYPE: PRT
```

<213> ORGANISM: Artificial Sequence
<220> FEATURE:
<223> OTHER INFORMATION: Synthesized Amino acid sequence of M6

<400> SEQUENCE: 15

```
Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Glu Leu Thr
        35                  40                  45

Pro Arg Gly Gly Glu Leu Ile Ala Tyr Leu Gly His Tyr Trp Arg Gln
50                  55                  60

Arg Leu Val Ala Asp Glu Leu Leu Pro Lys Cys Gly Cys Pro Gln Pro
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His His Gln Ala Asp Thr Ser Ser Pro Asp Pro Leu Phe Asn Pro Leu
        115                 120                 125

Lys Thr Gly Val Cys Gln Leu Asp Val Ala Asn Val Thr Arg Ala Ile
    130                 135                 140

Leu Glu Arg Ala Gly Gly Ser Ile Ala Asp Phe Thr Gly His Tyr Gln
145                 150                 155                 160

Pro Ala Phe Arg Glu Leu Glu Arg Val Leu Asn Phe Pro Gln Ser Pro
                165                 170                 175

Leu Cys Leu Lys Arg Glu Lys Gln Asp Glu Pro Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Glu Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Pro Gly Cys Glu Glu
    370                 375                 380

Arg Asn Ala Gln Gly Met Cys Ser Leu Ala Gly Phe Thr Gln Ile Val
```

Asn Glu Ala Arg Ile Pro Ala Cys Ser Leu
            405                 410

<210> SEQ ID NO 16
<211> LENGTH: 1233
<212> TYPE: DNA
<213> ORGANISM: Artificial Sequence
<220> FEATURE:
<223> OTHER INFORMATION: Synthesized Nucleotide sequence encoding M6

<400> SEQUENCE: 16

| | | | | | |
|---|---|---|---|---|---|
| cagtcagaac | cagagttgaa | gttggagtca | gtcgtcatcg | ttagtagaca | tggagttaga | 60 |
| gccctacaa | aggctaccca | gcttatgcaa | gatgttaccc | cagacgcttg | gccaacttgg | 120 |
| cctgtcaagt | gggagaact | tactcctaga | ggtggagagt | tgattgccta | ccttggtcat | 180 |
| tattggagac | aaagattggt | tgcagatgaa | ttgcttccaa | agtgtggttg | ccctcaacca | 240 |
| ggacaggttg | caattatcgc | tgatgttgat | gaaagaacta | gaaaaacagg | agaggctttt | 300 |
| gctgccggat | tggccccaga | ttgtgcaatc | actgttcatc | accaagccga | tacatcttcc | 360 |
| ccagacccctt | tgttcaaccc | tcttaagaca | ggagtctgtc | agttggatgt | tgccaatgtc | 420 |
| accagagcaa | ttttggaaag | agctggtgga | agtatcgccg | actttactgg | tcactaccaa | 480 |
| ccagctttca | gagaattgga | gagttctt | aactttccac | agtccccatt | gtgtcttaag | 540 |
| agagaaaagc | aagatgagcc | atgcagtttg | actcaggctc | ttccttctga | gttgaaagtt | 600 |
| tccgccgaca | acgtctcatt | gaccggagct | gtttctcttg | cctccatgtt | gactgaaatt | 660 |
| ttcttgcttc | aacaggctca | gggtatgcca | gagcctggtt | ggggaagaat | caccgatagt | 720 |
| catcagtgga | acactttgct | ttctttgcac | aatgctcaat | cgacttgct | tgagagaact | 780 |
| ccagaagttg | caagatccag | agctacacct | tgcttgatc | ttattaagac | cgcattgact | 840 |
| ccacatccac | tcaaaaaca | ggcttatgga | gttacattgc | ctacctctgt | cttgttcatc | 900 |
| gctggtcacg | acactaactt | ggcaaatctt | ggtggagctt | tggagcttaa | ctggacattg | 960 |
| ccaggtcaac | ctgataatac | cccacctggt | ggagaattgg | tttttgagag | atggagaaga | 1020 |
| ttgtcagaca | atagtcaatg | gattcaggtt | tccttggtct | tccaaacttt | gcaacagatg | 1080 |
| agagataaga | caccattgtc | acttaacacc | ccacctggtg | aagtcaaatt | gacacttcct | 1140 |
| ggatgtgaag | agagaaatgc | acaaggaatg | tgcagtcttg | ctggttttcac | ccaaatcgtc | 1200 |
| aatgaggcta | gaatccctgc | ttgttccttg | taa | | | 1233 |

<210> SEQ ID NO 17
<211> LENGTH: 410
<212> TYPE: PRT
<213> ORGANISM: Artificial Sequence
<220> FEATURE:
<223> OTHER INFORMATION: Synthesized Amino acid sequence of M7

<400> SEQUENCE: 17

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
                20                  25                  30

Thr Pro Asp Ala Trp Pro Thr Trp Pro Val Lys Leu Gly Glu Leu Thr
            35                  40                  45

Pro Arg Gly Gly Glu Leu Ile Ala Tyr Leu Gly His Tyr Trp Arg Gln
        50                  55                  60

Arg Leu Val Ala Asp Glu Leu Leu Pro Lys Cys Gly Cys Pro Gln Pro
 65                  70                  75                  80

Gly Gln Val Ala Ile Ile Ala Asp Val Asp Glu Arg Thr Arg Lys Thr
                 85                  90                  95

Gly Glu Ala Phe Ala Ala Gly Leu Ala Pro Asp Cys Ala Ile Thr Val
            100                 105                 110

His His Gln Ala Asp Thr Ser Ser Pro Asp Pro Leu Phe Asn Pro Leu
        115                 120                 125

Lys Thr Gly Val Cys Gln Leu Asp Val Ala Asn Val Thr Arg Ala Ile
130                 135                 140

Leu Glu Arg Ala Gly Gly Ser Ile Ala Asp Phe Thr Gly His Tyr Gln
145                 150                 155                 160

Pro Ala Phe Arg Glu Leu Glu Arg Val Leu Asn Phe Pro Gln Ser Pro
                165                 170                 175

Leu Cys Leu Lys Arg Glu Lys Gln Asp Glu Pro Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Pro Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Pro Gly Cys Glu Glu
370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 18
<211> LENGTH: 1233
<212> TYPE: DNA
<213> ORGANISM: Artificial Sequence
<220> FEATURE:
<223> OTHER INFORMATION: Synthesized Nucleotide sequence encoding M7

<400> SEQUENCE: 18
cagtcagaac cagagttgaa gttggagtca gtcgtcatcg ttagtagaca tggagttaga      60
gccactacaa aggctaccca gcttatgcaa gatgttaccc cagacgcttg gccaacttgg     120

-continued

```
cctgtcaagt tgggagaact tactcctaga ggtggagagt tgattgccta ccttggtcat    180
tattggagac aaagattggt tgcagatgaa ttgcttccaa agtgtggttg ccctcaacca    240
ggacaggttg caattatcgc tgatgttgat gaaagaacta gaaaaacagg agaggctttt    300
gctgccggat tggccccaga ttgtgcaatc actgttcatc accaagccga tacatcttcc    360
ccagacccct tgttcaaccc tcttaagaca ggagtctgtc agttggatgt tgccaatgtc    420
accagagcaa ttttggaaag agctggtgga agtatcgccg actttactgg tcactaccaa    480
ccagctttca gagaattgga gagagttctt aactttccac agtccccatt gtgtcttaag    540
agagaaaagc aagatgagcc atgcagtttg actcaggctc ttccttctga gttgaaagtt    600
tccgccgaca acgtctcatt gaccggagct gtttctcttg cctccatgtt gactgaaatt    660
ttcttgcttc aacaggctca gggtatgcca gagcctggtt ggggaagaat caccgatagt    720
catcagtgga cactttgctt tctttgcac aatgctcaat tcgacttgct tcagagaact    780
ccagaagttg caagaccaag agctacacct ttgcttgatc ttattaagac cgcattgact    840
ccacatccac ctcaaaaaca ggcttatgga gttacattgc ctacctctgt cttgttcatc    900
gctggtcacg cactaacttt ggcaaatctt ggtggagctt tggagcttaa ctggacattg    960
ccaggtcaac ctgataatac cccacctggt ggagaattgg ttttttgagag atggagaaga   1020
ttgtcagaca atagtcaatg gattcaggtt tccttggtct tccaaacttt gcaacagatg   1080
agagataaga caccattgtc acttaacacc ccacctggtg aagtcaaatt gacacttcct   1140
ggatgtgaag agagaaatgc acaaggaatg tgcagtcttg ctggtttcac ccaaatcgtc   1200
aatgaggcta gaatccctgc ttgttccttg taa                                 1233
```

<210> SEQ ID NO 19
<211> LENGTH: 410
<212> TYPE: PRT
<213> ORGANISM: Artificial Sequence
<220> FEATURE:
<223> OTHER INFORMATION: Synthesized Amino acid sequence of mutant

<400> SEQUENCE: 19

```
Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Glu Leu Thr
        35                  40                  45

Pro Arg Gly Gly Glu Leu Ile Ala Tyr Leu Gly His Tyr Trp Arg Gln
    50                  55                  60

Arg Leu Val Ala Asp Glu Leu Leu Pro Lys Cys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His His Gln Ala Asp Thr Ser Ser Pro Asp Pro Leu Phe Asn Pro Leu
        115                 120                 125

Lys Thr Gly Val Cys Gln Leu Asp Val Ala Asn Val Thr Arg Ala Ile
    130                 135                 140

Leu Glu Arg Ala Gly Gly Ser Ile Ala Asp Phe Thr Gly His Tyr Gln
145                 150                 155                 160
```

-continued

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Ala Gly Cys Glu Glu
    370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 20
<211> LENGTH: 419
<212> TYPE: PRT
<213> ORGANISM: Artificial Sequence
<220> FEATURE:
<223> OTHER INFORMATION: Synthesized Amino acid sequence of mutant

<400> SEQUENCE: 20

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Glu Leu Thr
        35                  40                  45

Pro Arg Gly Gly Glu Leu Ile Ala Tyr Leu Gly His Tyr Trp Arg Gln
    50                  55                  60

Arg Leu Val Ala Asp Glu Leu Pro Lys Cys Gly Cys Pro Gln Pro
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

```
His His Gln Ala Asp Thr Ser Ser Pro Asp Pro Leu Phe Asn Pro Leu
        115                 120                 125

Lys Thr Gly Val Cys Gln Leu Asp Val Ala Asn Val Thr Arg Ala Ile
130                 135                 140

Leu Glu Arg Ala Gly Gly Ser Ile Ala Asp Phe Thr Gly His Tyr Gln
145                 150                 155                 160

Pro Ala Phe Arg Glu Leu Arg Val Leu Asn Phe Pro Gln Ser Pro
                165                 170                 175

Leu Cys Leu Lys Arg Glu Lys Gln Asp Glu Pro Cys Ser Leu Thr Gln
                180                 185                 190

Ala Leu Pro Ser Glu Leu Lys Val Ser Ala Asp Asn Val Ser Leu Thr
                195                 200                 205

Gly Ala Val Ser Leu Ala Ser Met Leu Thr Glu Ile Phe Leu Leu Gln
210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
                260                 265                 270

Asp Leu Ile Lys Thr Ala Leu Thr Pro His Pro Pro Gln Lys Gln Ala
                275                 280                 285

Tyr Gly Val Thr Leu Pro Thr Ser Val Leu Phe Ile Ala Gly His Asp
                290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
                340                 345                 350

Val Phe Gln Thr Leu Gln Gln Met Arg Asp Lys Thr Pro Leu Ser Leu
                355                 360                 365

Asn Thr Pro Pro Gly Glu Val Lys Leu Thr Leu Pro Gly Cys Glu Glu
370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu Thr Cys Cys Thr Thr Gly
                405                 410                 415

Thr Ala Ala
```

PHYTASE MUTANT

CROSS REFERENCE TO RELATED APPLICATIONS

This application is a US National Phase application based upon PCT Application No. PCT/CN2020/074735 filed Feb. 11, 2020, which claims the priority of Chinese Patent Application No. 201910119308.0, filed to China National Intellectual Property Administration on Feb. 18, 2019, and titled with "PHYTASE MUTANT", and the disclosures of which are hereby incorporated by reference.

FIELD

The present disclosure relates to the field of biotechnology, specifically to a phytase mutant, a preparation method thereof and an application thereof, a DNA molecule encoding the phytase mutant, a vector and a host cell.

BACKGROUND

Phytase is a phosphatase that can hydrolyze phytic acid. It can degrade phytate phosphorus (inositol hexaphosphate) into inositol and inorganic phosphoric acid. This enzyme is divided into two categories: 3-phytase (EC. 3. 1. 3. 8) and 6-phytase (EC. 3. 1. 2. 6). Phytase is widely found in plants, animals and microorganisms, for example, higher plants such as corn and wheat, prokaryotic microorganisms such as *Bacillus subtilis, Pseudomonas, Lactobacillus*, and *Escherichia coli*, and eukaryotic microorganisms such as yeast, *Rhizopus*, and *Aspergillus*.

In the seeds of crops such as grains, beans, and oilseeds, the basic storage form of phosphorus is phytate phosphorus, the content of which is up to 1%-3%, which accounts for 60%-80% of the total phosphorus in plants. However, phosphorus in the form of phytate phosphorus is difficult to be used due to the lack of phytate-decomposing enzymes in monogastric animals, giving a utilization rate of only 0%-40%, which causes many problems. Firstly, the phosphorus sources in the feed can not be effectively used, and on the other hand, in order to meet the animal's requirements for phosphorus, inorganic phosphorus must be added to the feed, thus the cost of which increases. Secondly, the formation of high-phosphorus feces pollutes the environment. About 85% of the phytate phosphorus in the feed will be directly excreted by the animal, and the large amount of phytate phosphorus in the feces will seriously pollute the water and soil. In addition, phytate phosphorus is also an anti-nutritional factor. It will chelate with a variety of metal ions such as $Zn^{2+}$, $Ca^{2+}$, $Cu^{2+}$, and $Fe^{2+}$ as well as protein into insoluble complexes during the digestion and absorption process of the animal's gastrointestinal tract, reducing the effective utilization of these nutrients by the animal.

Phytase is used as a feed additive for monogastric animals, and its feeding effect has been confirmed worldwide. It can increase the utilization rate of phosphorus in plant feeds by 60%, reduce phosphorus excretion in feces by 40%, and at the same time reduce the anti-nutritional effects of phytic acid. Therefore, addition of phytase to feed is of great significance for improving the production efficiency of livestock and poultry industry and reducing the pollution of phytate phosphorus to the environment.

The industrially produced phytase mainly includes fungal phytase derived from *Aspergillus niger* and bacterial phytase derived from *Escherichia coli*. Among them, APPA, a phytase derived from *Escherichia coli*, has the characteristics of high specific activity and good stability in digestive tract. At present, it is mainly applied in the feed industry by directly adding to powder feed or spray coating pellet feed.

There is a short period of high temperature of 80-90° C. in the production process of pellet feed, and bacterial phytase APPA has poor thermal stability. When its aqueous solution is kept at 70° C. for 5 minutes, the remaining enzyme activity is less than 30%, and when it is directly added to animal feed for pelleting, the remaining enzyme activity is generally less than 20%, which limits the application of APPA phytase in pellet feed. The method of spray coating the phytase liquid onto the feed after pelleting not only increases the equipment cost, but also fails to guarantee the stability of the enzyme preparation and the uniformity of the distribution in the feed. Therefore, improving the thermal stability of phytase has important practical significance for the current phytase used in feed.

SUMMARY

In view of this, the present disclosure provides a phytase mutant (a mutant protein) having improved heat resistance, thereby facilitating the wide application of phytase in the field of feed.

In order to achieve the above-mentioned purpose of the present disclosure, the present disclosure provides the following technical solutions.

The present disclosure relates to a phytase mutant, which comprises an amino acid sequence having at least 90% identity with SEQ ID NO: 1, and comprises an amino acid substitution compared with SEQ ID NO: 1 at at least one position selected from the group consisting of: 36, 69, 89, 91, 111, 202, 213, 225, 238, 243, 253, 258, and 266.

In some embodiments of the present disclosure, the mutant comprises an amino acid sequence having at least 91%, 92%, 93%, 94%, 95%, 96%, 97%, 98%, or at least 99% identity with SEQ ID NO: 1.

In some more particular embodiments, the mutant comprises an amino acid sequence having at least 99.1%, 99.2%, 99.3%, 99.4%, 99.5%, 99.6%, 99.7%, 99.8%, or at least 99.9% identity with SEQ ID NO: 1.

In some embodiments of the present disclosure, the mutant comprises at least one amino acid substitution selected from the group consisting of A36P, D69F, D69Q, V89T, E91Q, T111P, A202P, L213F, L213W, Q225Y, T238R, W243V, W243L, Q253Y, Q258E, and S266P.

In some embodiments of the present disclosure, the mutant comprises an amino acid substitution or a combination selected from the group consisting of:
Q258E,
Q258E/S266P,
V89T/Q258E,
E91Q/Q258E,
Q225Y/Q258E,
Q253Y/Q258E,
V89T/E91Q/Q258E,
V89T/Q225Y/Q258E,
V89T/Q253Y/Q258E,
V89T/Q258E/S266P,
E91Q/Q225Y/Q258E,
E91Q/Q253Y/Q258E,
E91Q/Q258E/S266P,
Q225Y/Q253Y/Q258E,
Q225Y/Q258E/S266P,
V89T/E91Q/Q225Y/Q258E,
V89T/E91Q/Q253Y/Q258E,
V89T/E91Q/Q258E/S266P, E91Q/Q225Y/Q253Y/Q258E,
E91Q/Q225Y/Q258E/S266P,
V89T/Q225Y/Q253Y/Q258E,
V89T/Q225Y/Q258E/S266P,
E91Q/Q225Y/Q253Y/Q258E,
E91Q/Q225Y/Q258E/S266P,
E91Q/Q253Y/Q258E/S266P,
V89T/Q253Y/Q258E/S266P,
V89T/E91Q/Q225Y/Q253Y/Q258E,
V89T/Q225Y/Q253Y/Q258E/S266P,
V89T/E91Q/Q253Y/Q258E/S266P,
V89T/E91Q/Q225Y/Q258E/S266P,
E91Q/Q225Y/Q253Y/Q258E/S266P,
V89T/E91Q/Q225Y/Q253Y/Q258E/S266P,
S266P,
V89T/S266P,
E91Q/S266P,
Q225Y/S266P,
Q253Y/S266P,
V89T/E91Q/S266P,
V89T/Q225Y/S266P,
V89T/Q253Y/S266P,
E91Q/Q225Y/S266P,
E91Q/Q253Y/S266P,
Q225Y/Q253Y/S266P,
V89T/E91Q/Q225Y/S266P,
V89T/E91Q/Q253Y/S266P,
V89T/Q225Y/Q253Y/S266P,
V89T/E91Q/Q225Y/Q253Y/S266P,
V89T/E91Q,
V89T/Q253Y,
E91Q/Q253Y,
V89T/E91Q/Q253Y,
V89T/E91Q/Q225Y,
V89T/Q225Y/Q253Y,
E91Q/Q225Y/Q253Y,
V89T/E91Q/Q225Y/Q253Y,
V89T/E91Q/A202P/Q253Y,
V89T/E91Q/L213F/Q253Y,
V89T/E91Q/L213W/Q253Y,
V89T/E91Q/W243V/Q253Y,
V89T/E91Q/W243L/Q253Y,
D69F/V89T/E91Q/Q253Y,
D69Q/V89T/E91Q/Q253Y,
V89T/E91Q/T111P/Q253Y,
V89T/E91Q/T238R/Q253Y,
A36P/V89T/E91Q/Q253Y,
V89T/E91Q/A202P/L213F/Q253Y,
V89T/E91Q/A202P/L213W/Q253Y,
V89T/E91Q/A202P/W243V/Q253Y,
V89T/E91Q/A202P/W243Q/Q253Y,
V89T/E91Q/L213F/W243V/Q253Y,
V89T/E91Q/L213W/W243L/Q253Y,
V89T/E91Q/L213F/W243L/Q253Y,
V89T/E91Q/L213W/W243V/Q253Y,
V89T/E91Q/A202P/L213F/W243V/Q253Y,
V89T/E91Q/A202P/L213W/W243L/Q253Y,
V89T/E91Q/A202P/L213F/W243L/Q253Y,
V89T/E91Q/A202P/L213W/W243V/Q253Y,
V89T/E91Q/A202P/Q225Y/Q253Y,
V89T/E91Q/L213F/Q225Y/Q253Y,
V89T/E91Q/L213W/Q225Y/Q253Y,
V89T/E91Q/W243V/Q225Y/Q253Y,
V89T/E91Q/W243L/Q225Y/Q253Y,
D69F/V89T/E91Q/Q225Y/Q253Y,
D69Q/V89T/E91Q/Q225Y/Q253Y,
V89T/E91Q/T111P/Q225Y/Q253Y,
V89T/E91Q/T238R/Q225Y/Q253Y,
A36P/V89T/E91Q/Q225Y/Q253Y,
V89T/E91Q/A202P/Q225Y/Q253Y/Q258E/S266P,
V89T/E91Q/L213F/Q225Y/Q253Y/Q258E/S266P,
V89T/E91Q/L213W/Q225Y/Q253Y/Q258E/S266P,
V89T/E91Q/W243V/Q225Y/Q253Y/Q258E/S266P,
V89T/E91Q/W243L/Q225Y/Q253Y/Q258E/S266P,
D69F/V89T/E91Q/Q225Y/Q253Y/Q258E/S266P,
D69Q/V89T/E91Q/Q225Y/Q253Y/Q258E/S266P,
V89T/E91Q/T111P/Q225Y/Q253Y/Q258E/S266P,
V89T/E91Q/T238R/Q225Y/Q253Y/Q258E/S266P,
A36P/V89T/E91Q/Q225Y/Q253Y/Q258E/S266P,
V89T/E91Q/A202P/L213F/Q225Y/Q253Y/Q258E/S266P,
V89T/E91Q/A202P/L213W/Q225Y/Q253Y/Q258E/S266P,
V89T/E91Q/A202P/Q225Y/W243V/Q253Y/Q258E/S266P,
V89T/E91Q/A202P/Q225Y/W243L/Q253Y/Q258E/S266P,
V89T/E91Q/L213F/Q225Y/W243V/Q253Y/Q258E/S266P,
V89T/E91Q/L213W/Q225Y/W243L/Q253Y/Q258E/S266P,
V89T/E91Q/L213F/Q225Y/W243L/Q253Y/Q258E/S266P,
V89T/E91Q/L213W/Q225Y/W243V/Q253Y/Q258E/S266P,
V89T/E91Q/A202P/L213F/Q225Y/W243V/Q253Y/Q258E/S266P,
V89T/E91Q/A202P/L213W/Q225Y/W243L/Q253Y/Q258E/S266P,
V89T/E91Q/A202P/L213F/Q225Y/W243L/Q253Y/Q258E/S266P,
V89T/E91Q/A202P/L213W/Q225Y/W243V/Q253Y/Q258E/S266P,
A202P,
L213F,
L213W,
W243V,
W243L,
D69Q,
D69F,
T111P,
T238R,
A36P,
A202P/L213F,
A202P/L213W,
A202P/W243L,
A202P/W243V,
A202P/L213F/W243L,
A202P/L213F/W243V,
A202P/L213W/W243V, and
A202P/L213W/W243L.

In some embodiments of the present disclosure, the mutant further comprises at least an amino acid substitution selected from the group consisting of A25F, D35Y, W46E, Q62W, G70E, A73P, K75C, S80P, T114H, N126D, N137V, D142R, S146E, R159Y, T161P, N176P, K180N, S187P, V211W, Q253V, Y255D, T327Y, and A380P.

In preferred embodiments of the present disclosure, the amino acid substitution is a combination selected from the group consisting of:
W46E/Q62W/G70E/A73P/K75C/T114H/N137V/D142R/S146E/R159Y/Y255D,
A25F/W46E/Q62W/G70E/A73P/K75C/T114H/N137V/D142R/S146E/R159Y/Y255D,
W46E/Q62W/G70E/A73P/K75C/T114H/N137V/D142R/S146E/R159Y/Y255D/A380P,
A25F/W46E/Q62W/G70E/A73P/K75C/T114H/N137V/D142R/S146E/R159Y/Y255D/A380P, W46E/Q62W/G70E/A73P/K75C/S80P/T114H/N137V/ D142R/S146E/R159Y/N176P/S187P/Y2 55D/A380P,
A25F/W46E/Q62W/G70E/A73P/K75C/S80P/T114H/ N137V/D142R/S146E/R159Y/N176P/S18 7P/Y255D/ A380P,
W46E/Q62W/G70E/A73P/K75C/S80P/T114H/N137V/ D142R/S146E/R159Y/T161P/N176P/S18 7P/Y255D/ A380P, and
A25F/W46E/Q62W/G70E/A73P/K75C/S80P/T114H/ N137V/D142R/S146E/R159Y/T161P/N17 6P/S187P/ Y255D/A380P.

The present disclosure also relates to a DNA molecule encoding the phytase mutant.

The present disclosure also relates to a recombinant expression vector comprising the DNA molecule.

The present disclosure also relates to a host cell comprising the recombinant expression vector.

After transforming the vectors into a host cell, the heat resistance of the recombinant phytase mutants is significantly improved.

In some embodiments of the present disclosure, the host cell is Pichia pastoris.

In some embodiments of the present disclosure, the host cell is Trichoderma reesei.

The present disclosure also provides a method for producing the phytase mutant, comprising:

Step 1: Generating a DNA molecule encoding a phytase mutant, wherein the phytase mutant comprises an amino acid sequence having at least 90% identity with SEQ ID NO: 1, and comprises an amino acid substitution compared with SEQ ID NO: 1 at at least one position selected from the group consisting of: 36, 69, 89, 91, 111, 202, 213, 225, 238, 243, 253, 258, and 266.

Step 2: Fusing the DNA molecule obtained in step 1 with an expression vector to construct a recombinant expression vector and transforming the vector into a host cell;

Step 3: Inducing the expression of the fusion protein in the host cells comprising the recombinant expression vector, isolating and purifying the expressed fusion protein.

In some embodiments of the present disclosure, the phytase mutant described in step 1 comprises at least one amino acid substitution selected from the group consisting of A36P, D69F, D69Q, V89T, E91Q, T111P, A202P, L213F, L213W, Q225Y, T238R, W243V, W243L, Q253Y, Q258E, and S266P In some embodiments of the present disclosure, the host cell described in step 2 is Pichia pastoris.

In some embodiments of the present disclosure, the host cell described in step 2 is Trichoderma reesei.

The present disclosure also provides use of the phytase mutant in feed.

Based on wild-type phytase APPA, the present disclosure provides a phytase mutant comprising a single mutation site of Q258E, 5266P, or a combination of two mutation sites of Q258E/S266P. After treatment at 65° C. for 3 minutes, the phytase mutants have a residual enzyme activity of 17.62%-31.80%, which is 59.9%-188.6% higher than that of the wild-type phytase APPA, showing that the heat resistance is significantly improved, which is beneficial to the wide application of phytase in feed industry.

DETAILED DESCRIPTION

The present disclosure discloses a phytase mutant, a preparation method thereof and an application thereof, a DNA molecule encoding the phytase mutant, a vector, and a host cell. Those skilled in the art can be achieved by learning from the contents of the present disclosure and appropriately improving the process parameters. The method and the application of the present disclosure have been described through the preferred embodiments, and it is obvious that the method and application described herein may be changed or appropriately modified and combined without departing from the content, spirit and scope of the present disclosure.

In the present disclosure, the nomenclature used to define amino acid positions is based on the amino acid sequence of E. coli phytase deposited in Genbank under No. ABF60232, which is given in the sequence listing as SEQ ID NO: 1 (Amino acids 1-410). Therefore, in this context, SEQ ID NO: 1 is used for numbering the amino acid positions, starting at Q1 (Gln1) and ending at L410 (Leu410). SEQ ID NO: 1 serves as the standard for position numbering and therefore serves as the basis for nomenclature.

The present disclosure employs conventional techniques and methods used in the fields of genetic engineering and molecular biology, such as the methods described in MOLECULAR CLONING: A LABORATORY MANUAL, 3nd Ed. (Sambrook, 2001) and CURRENT PROTOCOLS IN MOLECULAR BIOLOGY (Ausubel, 2003). These general references provide definitions and methods known to those skilled in the art. However, those skilled in the art can adopt other conventional methods, experimental schemes, and reagents in the field on the basis of the technical solutions described in the present disclosure, and are not limited to the limitations of the particular embodiments of the present disclosure. For example, the present disclosure can choose the following experimental materials and reagents.

Strains and vectors: E. coli DH5α, Pichia pastoris GS115, vector pPIC9k, Amp, and G418 were purchased from Invitrogen.

Enzymes and kits: PCR enzymes and ligases were purchased from Takara, restriction enzymes were purchased from Fermentas, plasmid extraction kits and gel purification recovery kits were purchased from Omega, and GeneMorph II random mutagenesis kits were purchased from Beijing Biomars Biological Technology Co., Ltd.

Medium formulas:

E. coli medium (LB medium): 0.5% yeast extract, 1% peptone, 1% NaCl, pH 7.0;

Yeast medium (YPD medium): 1% yeast extract, 2% peptone, 2% glucose;

Yeast screening medium (MD plate): 2% peptone, 2% agarose;

BMGY medium: 2% peptone, 1% yeast extract, 100 mM potassium phosphate buffer (pH 6.0), 1.34% YNB, $4 \times 10^{-5}$% biotin, 1% glycerol;

BMMY medium: 2% peptone, 1% yeast extract, 100 mM potassium phosphate buffer (pH 6.0), 1.34% YNB, $4 \times 10^{-5}$% biotin, 0.5% methanol;

LB-AMP medium: 0.5% yeast extract, 1% peptone, 1% NaCl, 100 μg/mL ampicillin, pH 7.0;

LB-AMP plate: 0.5% yeast extract, 1% peptone, 1% NaCl, 1.5% agar, 100 μg/mL ampicillin, pH 7.0;

Upper layer medium (plate): 0.1% $MgSO_4$, 1% $KH_2PO_4$, 0.6% $(NH_4)_2SO_4$, 1% glucose, 18.3% sorbitol, 0.35% agarose;

Lower layer medium (plate): 2% glucose, 0.5% $(NH_4)_2SO_4$, 1.5% $KH_2PO_4$, 0.06% $MgSO_4$, 0.06% $CaCl_2$, 1.5% agar.

The present disclosure will be further illustrated below in conjunction with examples.

Example 1 Screening of Heat-Resistant Mutants

The amino acid sequence of wild-type phytase APPA derived from *E. coli* is shown in SEQ ID NO: 1, and its coding nucleotide sequence is shown in SEQ ID NO: 2. In order to improve the heat resistance of phytase APPA, the inventors conducted a protein structure analysis on phytase. The protein has two domains: domain 1 constituted by 134 amino acid residues at N-terminal and 152 amino acid residues at C-terminal together, and domain 2 constituted by the remaining 124 amino acid residues in the middle. The conserved sequence and activity center are both located in domain 1. The method is to mutate the gene without damage to the secondary structure and activity center of the protein.
1.1 Design of PCR Primer APPA-F1 and APPA-R1:

APPA-F1: GGCGAATTC CAGTCAGAACCAGAGTT-GAAGTT (The restriction enzyme EcoRI recognition site is underlined), as shown in SEQ ID NO: 3; and APPA-R1: ATAGCGGCCGC TTACAAGGAACAA-GCAGGGAT (The restriction enzyme NotI recognition site is underlined), as shown in SEQ ID NO: 4.

APPA gene (SEQ ID NO: 2) was served as the template, and the above primers were used to perform PCR amplification by GeneMorph II Random Mutation PCR Kit (Stratagene), followed by recovering the PCR product from gel. After digested with EcoRI and NotI, the PCR product was ligated into pET21a vector that was subjected to the same digestion. The ligation product was transformed into *E. coli* BL21 (DE3) and then the cells were spread on LB+Amp plate for culturing upside down at 37° C. After the transformants appeared, they were picked one by one with toothpicks and transferred to a 96-well plate, with each well added with 150 μl of LB+Amp medium containing 0.1 mM IPTG, followed by culture at 220 rpm at 37° C. for about 6 hours. Afterwards, the culture was centrifuged and the supernatant was discarded. The bacteria cells were resuspended in buffer, and repeatedly frozen and thawed to obtain *E. coli* cell lysate containing phytase.

40 μl of lysate was transferred to two new 96-well plates each, and one 96-well plate was treated at 75° C. for 5 min; then 80μl substrate was added to each of the two 96-well plates allowing them react at 37° C. for 30 min, and then 80 μl of termination solution (ammonium vanadate:ammonium molybdate:nitric acid=1:1:2) was added. The content of inorganic phosphorus generated during the reaction was determined. Different mutants remained different activities after high temperature treatment.

Experimental results show that some mutations have no effect on the heat resistance of phytase APPA, some mutations even make its heat resistance or enzyme activity worse, and some mutations can improve APPA's temperature tolerance but also alter its enzymatic properties significantly, all these did not meet the requirements. In the end, the inventors found mutation sites that can significantly improve APPA's heat resistance without affecting its enzyme activity and enzymatic properties are: A36P, D69F, D69Q, V89T, E91Q, T111P, A202P, L213F, L213W, Q225Y, T238R, W243V, W243L, Q253Y, Q258E, and S266P.

On the basis of phytase APPA, the present disclosure provides a phytase mutant comprising at least 1, at least 2, at least 3, at least 4, at least 5, at least 6, at least 7, at least 8, at least 9, at least 10, at least 11, at least 12, or at least 13 mutation sites selected from the group consisting of A36P, D69F, D69Q, V89T, E91Q, T111P, A202P, L213F, L213W, Q225Y, T238R, W243V, W243L, Q253Y, Q258E, and S266P.

The mutant further comprises at least an amino acid substitution selected from the group consisting of A25F, D35Y, W46E, Q62W, G70E, A73P, K75C, S80P, T114H, N126D, N137V, D142R, S146E, R159Y, T161P, N176P, K180N, S187P, V211W, Q253V, Y255D, T327Y, and A380P.

The mutant further comprises a combination of mutation sites, which is selected from the group consisting of:
W46E/Q62W/G70E/A73P/K75C/T114H/N137V/D142R/S146E/R159Y/Y255D,
A25F/W46E/Q62W/G70E/A73P/K75C/T114H/N137V/D142R/S146E/R159Y/Y255D,
W46E/Q62W/G70E/A73P/K75C/T114H/N137V/D142R/S146E/R159Y/Y255D/A380P,
A25F/W46E/Q62W/G70E/A73P/K75C/T114H/N137V/D142R/S146E/R159Y/Y255D/A380P,
W46E/Q62W/G70E/A73P/K75C/S80P/T114H/N137V/D142R/S146E/R159Y/N176P/S187P/Y2 55D/A380P,
A25F/W46E/Q62W/G70E/A73P/K75C/S80P/T114H/N137V/D142R/S146E/R159Y/N176P/S18 7P/Y255D/A380P,
W46E/Q62W/G70E/A73P/K75C/S80P/T114H/N137V/D142R/S146E/R159Y/T161P/N176P/S187P/Y255D/A380P, and
A25F/W46E/Q62W/G70E/A73P/K75C/S80P/T114H/N137V/D142R/S146E/R159Y/T161P/N17 6P/S187P/Y255D/A380P.

On the basis of phytase APPA, the present disclosure provides mutants comprising a single mutation site of Q258E or S266P or a combination of Q258E/S266P, named M1, M2 and M3, respectively.

On the basis of the phytase mutants M1 and M2, the present disclosure provides phytase mutants further comprising a combination of mutation sites W46E/Q62W/G70E/A73P/K75C/T114H/N137V/D142R/S146E/R159Y/Y255D, named M4 and M5, respectively.

On the basis of the phytase mutants M1 and M2, the present disclosure provides phytase mutants further comprising a combination of mutation sites W46E/Q62W/G70E/A73P/K75C/S80P/T114H/N137V/D142R/S146E/R159Y/T161P/N176P/S18 7P/Y255D/A380P, named M6 and M7, respectively.

The amino acid sequences of the mutants M1, M2, M3, M4, M5, M6, and M7 are SEQ ID NO: 5, SEQ ID NO: 7, SEQ ID NO: 9, SEQ ID NO: 11, SEQ ID NO: 13, SEQ ID NO: 15, and SEQ ID NO: 17, respectively.

The coding nucleotide sequences of the mutants M1, M2, M3, M4, M5, M6, and M7 are SEQ ID NO: 6, SEQ ID NO: 8, SEQ ID NO: 10, SEQ ID NO: 12, SEQ ID NO: 14, SEQ ID NO: 16, and SEQ ID NO: 18, respectively.

Example 2 Expression of Phytase Mutants in *Pichia Pastoris*

According to the codon preference of *Pichia pastoris*, the gene sequence of APPA as shown in SEQ ID NO: 2 and that of the mutants were optimized and synthesized, and two restriction sites of enzymes EcoRI and NotI were added to the 5' and 3' ends of the synthetic sequence.
2.1 Construction of Expression Vector The gene sequences of synthesized APPA and the mutants were digested with EcoRI and NotI respectively, and then ligated into the pPIC-9K vector (after the same digestion) at 16° C. overnight. The ligation product was then transformed into E. coli DH5a and the cells were spread on LB+Amp plate for culturing upside down at 37° C. After the transformants appeared, they were subjected to colony PCR (reaction system: picked single clones as template, 0.5 µl of rTaq DNA polymerase, 2.0 µL of 10×Buffer, 2.0 µL of dNTPs (2.5 mM), 0.5 µl of 5'AOX primer (10 mM), 0.5 µl of 3'AOX primer, 14.5 µL of ddH$_2$O, reaction program: 95° C. pre-denaturation for 5 min; 30 cycles of 94° C. for 30 sec, 55° C. for 30 sec, and 72° C. for 2 min; and 72° C. for 10 min). The positive clones were verified, and the correct recombinant expression plasmid was obtained after sequencing verification.

2.2 Construction of Engineered *Pichia pastoris* Strain 2.2.1 Preparation of Yeast Competent Cells The *Pichia pastoris* GS115 strain was activated on an YPD plate. After culturing at 30° C. for 48 hours, single clones of the activated GS115 were inoculated into 6 mL of YPD liquid medium at 220 rpm at 30° C. for about 12 hours. After that, the cells were transferred into an Erlenmeyer flask containing 30 mL of YPD liquid medium and cultured at 220 rpm at 30° C. for about 5 hours. The cell density was detected by an spectrophotometer. After the OD600 value was in the range of 1.1-1.3, the cells were subjected to centrifugation at 4° C., 9,000 rpm for 2 min, and 4 mL of cells was collected in a sterilized EP tube. The supernatant was gently discarded, and the remaining supernatant was absorbed with sterile filter paper. Subsequently, the cells were resuspended in 1 mL of pre-cooled sterilized water, followed by centrifugation at 4° C., 9,000 rpm for 2 min. The supernatant was gently discarded, and the cells were washed with 1 mL sterile water for another time, followed by centrifugation at 4° C., 9,000 rpm for 2 min. The supernatant was gently discarded, and the cells were resuspended in 1 mL of pre-cooled sorbitol (1 mol/L), followed by centrifugation at 4° C., 9,000 rpm for 2 min. The supernatant was gently discarded, and the cells were resuspended in 100-150 µl of the pre-cooled sorbitol (1 mol/L) gently.

2.2.2 Transformation and Screening

The expression plasmids constructed in 2.1 were linearized with SacI. After the linearized fragments were purified and recovered, they were transformed into *Pichia pastoris* GS115 by electroporation. The recombinant strains of *Pichia pastoris* were screened on MD plates, and then transformants having multiple copies were screened on an YPD plate containing different concentrations of geneticin (0.5-8 mg/mL).

The obtained transformants were transferred to BMGY medium and cultured with shaking at 30° C. and 250 rpm for 1d; then transferred to BMMY medium and cultured with shaking at 30° C. and 250 rpm. 0.5% methanol was added every day to induce expression for 4 days. After centrifugation at 9,000 rpm for 10 min to remove the cells, the fermentation supernatants containing wild-type phytase APPA and phytase mutants were obtained respectively.

(1) Definition of Phytase Enzyme Activity Unit

Under the conditions of a temperature of 37° C. and a pH of 5.0, 1 nmol of inorganic phosphorus released from 5.0 mmol/L sodium phytate per minute is a unit of phytase enzyme activity, expressed in U.

(2) Determination Method for Phytase Enzyme Activity

In each of the two 25 mL colorimetric tubes A and B, 1.8 mL of acetic acid buffer (pH 5.0) and 0.2 mL of sample (reaction solution) were added and mixed well, and pre-heated at 37° C. for 5 min. 4 mL of the substrate solution was added to tube A, while 4 mL of stop solution (termination solution) to tube B. Both were mixed well and allowed to react at 37° C. for 30 min. After the reaction was over, 4 mL of stop solution was added to tube A while 4 mL of substrate solution to tube B. Both were mixed well and allowed to stand for 10 min. The absorbance at 415 nm wavelength was measured. Each sample was tested in triplicate for the average of the absorbance value, and the phytase enzyme activity was calculated using the regression linear equation through the standard curve.

Enzyme activity $X = F \times C/(m \times 30)$

Wherein: X—enzyme activity unit, U/g (mL);
F—Total dilution factor of the sample solution before the reaction;
C—Enzyme activity calculated by the linear regression equation based on the absorbance of the actual sample solution, U;
m—Mass or volume of the sample, g/mL; and
30—Reaction time.

The phytase enzyme activity was measured on the fermentation supernatants of the constructed recombinant strains of *Pichia pastoris* using the above methods.

Example 3 Expression of Phytase Mutants in *Trichoderma Reesei*

According to the codon preference of *Trichoderma*, the gene sequence of APPA as shown in SEQ ID NO: 2 and that of the mutants were optimized and synthesized, and two restriction sites of enzymes KpnI and MluI were added to the 5' and 3' ends of the synthetic sequence.

3.1 Construction of Expression Vector

The synthesized phytase gene fragment and pSC1G vector were digested with restriction enzymes KpnI and MluI (Fermentas) respectively, and the digested product was purified using a gel purification kit. The digested products of the above phytase gene and the pSC1G vector were ligated using T$_4$ DNA ligase (Fermentas) and transformed into *E. coli* Trans5α (Transgen). Ampicillin was used for selection, and the clone was sequenced (Invitrogen) for verification. After sequencing verification, a recombinant plasmid containing the phytase gene was obtained.

3.2 Construction of Recombinant Strains of *Trichoderma reesei*

(1) Preparation of Protoplasts

The host *Trichoderma reesei* UE spore suspension was inoculated on a PDA plate, and cultured at 30° C. for 6 days. After the spores were abundant, a colony of about 1 cm×1 cm was cut and transferred into liquid culture medium containing 120 mL of YEG+U (0.5% yeast powder, 1% glucose, and 0.1% uridine), and then cultured at 30° C. with shaking 220 rpm for 14-16 h.

The mycelium was collected by filtration with sterile gauze, and washed once with sterile water. The mycelium was transferred into an Erlenmeyer flask containing 20 mL of 10 mg/mL lysing enzyme solution (Sigma L1412) at 30° C., 90 rpm for 1-2 h. The progress of protoplast transformation was observed and detected with a microscope.

20 mL of pre-cooled 1.2 M sorbitol (1.2 M sorbitol, 50 mM Tris-Cl, 50 mM CaCl$_2$) was added into the above Erlenmeyer flask, which was then shaken gently. Afterwards, filtration was performed with a sterile Miracloth filter cloth to collect the filtrate, which was then subjected to centrifugation at 3,000 rpm, 4° C. for 10 min and the supernatant was discarded. Then, 5 mL of pre-cooled 1.2 M sorbitol solution was added to suspend the cells, which was then subjected to centrifugation at 3,000 rpm, 4° C. for 10 min and the supernatant was discarded. Then, an appropriate amount of pre-cooled 1.2 M sorbitol was added to suspend and aliquot (200 μL/tube, with a concentration of protoplasts of $10^8$/mL).

(2) Transformation of expression vector

The following operations were all performed on ice. 10 μg of the recombinant plasmids constructed above was added to a 7 mL sterile centrifuge tube containing 200 μL of protoplast solution, and then 50 μL of 25% PEG (25% PEG, 50 mM Tris-Cl, 50 mM $CaCl_2$) was added. The mixture was mixed well by flicking the bottom of the tube, and placed on ice for 20 minutes. Then 2 mL of 25% PEG was added, mixed well and allowed to stand for 5 minutes at room temperature. Then 4 mL of 1.2 M sorbitol was added and mixed gently. The resultant was poured into the upper medium that had been melted and kept at 55° C. After mixed gently, it was spread on the prepared lower medium plate and cultured at 30° C. for 5-7 days until transformants appeared. The transformants were picked and transferred to the lower medium plate for re-screening, and the strains with smooth colony edges were the positive transformants.

According to the above method, the inventors obtained the engineered strains of Trichoderma reesei that express APPA or the above phytase mutants.

(3) Fermentation Verification and Determination of Enzyme Activity

The engineered strains of Trichoderma reesei obtained by the above construction method were inoculated into PDA solid plates, and cultured upside down in a constant temperature incubator at 30° C. for 6-7 days. After the spores were abundant, two hypha blocks with a diameter of 1 cm were inoculated separately into a 250 mL Erlenmeyer flask containing 50 mL of fermentation medium (1.5% glucose, 1.7% lactose, 2.5% corn steep liquor, 0.44% $(NH_4)_2SO_4$, 0.09% $MgSO_4$, 2% $KH_2PO_4$, 0.04% $CaCl_2$, 0.018% Tween-80, and 0.018% trace elements), and cultured at 30° C. for 48 hours, followed by being cultured at 25° C. for 48 hours. The fermentation broth was centrifuged to obtain fermentation supernatants containing phytase APPA or the above-mentioned phytase mutants respectively.

The method described in Example 2 was used to determine the phytase enzyme activity of the fermentation supernatant of the constructed Trichoderma reesei recombinant strains.

Example 4 Thermal Stability Analysis

The fermentation supernatants of the recombinant strains expressing the phytase mutants obtained above were diluted by 10 times with pH 5.0, 0.25 M sodium acetate buffer solution preheated for 10 min. Then the diluted samples were treated respectively as follows: 65° C. for 3 minutes, 80° C. for 4 minutes, or 85° C. for 5 minutes. After that, the samples were cooled to room temperature, and the phytase enzyme activities after heat treatment were measure respectively. The residual enzyme activity was calculated based on that the enzyme activity of the untreated sample is 100%. The results are shown in Tables 1-3.

Residual enzyme activity (%)=enzyme activity of untreated sample/enzyme activity of heat-treated sample×100%.

TABLE 1

Comparison of residual enzyme activity of phytase

| Phytase | Residual enzyme activity after treatment at 65° C. for 3 min |
|---|---|
| APPA | 11.02% |
| M1 | 31.80% |
| M2 | 17.62% |
| M3 | 23.60% |

The results in Table 1 show that after the treatment at 65° C. for 3 min, the phytase mutants M1, M2, and M3 comprising Q258E and/or S266P mutation sites provided by the present disclosure have a residual enzyme activity of 17.62%-31.80%, which is 59.9%-188.6% higher than the residual enzyme activity of phytase APPA. This indicates that the Q258E and/or S266P mutations on the basis of phytase APPA can significantly improve its heat resistance.

TABLE 2

Comparison of residual enzyme activity of phytase

| Phytase | Residual enzyme activity after treatment at 80° C. for 4 min |
|---|---|
| APPA + W46E/Q62W/G70E/ A73P/K75C/T114H/N137V/ D142R/S146E/R159Y/Y255D | 19.98% |
| M4 | 44.39% |
| M5 | 49.44% |

As a control, the present disclosure provides a phytase mutant comprising a combination of mutation sites W46E/Q62W/G70E/A73P/K75C/T114H/N137V/D142R/S146E/R159Y/Y255D based on the phytase APPA, and its amino acid sequence is shown in SEQ ID NO: 19. The results in Table 2 show that after the treatment at 80° C. for 4 min, the residual enzyme activity of mutants M4 and M5, which are further comprising a single mutation site of Q258E and S266P compared with the control mutant, is increased by 122.2%-147.4%, demonstrating that the heat resistance has been significantly improved.

TABLE 3

Comparison of residual enzyme activity of phytase

| Phytase | Residual enzyme activity after treatment at 85° C. for 5 min |
|---|---|
| APPA + W46E/Q62W/G70E/A73P/ K75C/S80P/T114H/N137V/D142R/ S146E/R159Y/T161P/N176P/ S187P/Y255D/A380P | 26.26% |
| M6 | 38.24% |
| M7 | 47.80% |

As a control, the present disclosure provides a phytase mutant comprising a combination of mutation sites W46E/Q62W/G70E/A73P/K75C/S80P/T114H/N137V/D142R/S146E/R159Y/T161P/N176P/S18 7P/Y255D/A380P based on phytase APPA, and its amino acid sequence is shown in SEQ ID NO: 20. The results in Table 3 show that after the treatment at 85° C. for 5 min, the residual enzyme activity of mutants M6 and M7, which are further comprising a single mutation site of Q258E and S266P compared with the control mutant, is increased by 45.6%-82.0%, demonstrating that the heat resistance has been significantly improved.

In summary, the mutation sites Q258E and S266P provided by the present disclosure can significantly improve the heat resistance of phytase, thereby facilitating the application of phytase in feed industry.

The invention claimed is:

1. A phytase mutant, wherein the mutant comprises an amino acid sequence having at least 90% identity with SEQ ID NO: 1, and the mutant comprises an amino acid substitution or a combination selected from the group consisting of:
Q258E,
Q258E/S266P,
V89T/Q258E,
E91Q/Q258E,
Q225Y/Q258E,
Q253Y/Q258E,
V89T/E91Q/Q258E,
V89T/Q225Y/Q258E,
V89T/Q253Y/Q258E,
V89T/Q258E/S266P,
E91Q/Q225Y/Q258E,
E91Q/Q253Y/Q258E,
E91Q/Q258E/S266P,
Q225Y/Q253Y/Q258E,
Q225Y/Q258E/S266P,
V89T/E91Q/Q225Y/Q258E,
V89T/E91Q/Q253Y/Q258E,
V89T/E91Q/Q258E/S266P,
E91Q/Q225Y/Q253Y/Q258E,
E91Q/Q225Y/Q258E/S266P,
V89T/Q225Y/Q253Y/Q258E,
V89T/Q225Y/Q258E/S266P,
E91Q/Q225Y/Q258E/S266P,
E91Q/Q253Y/Q258E/S266P,
V89T/Q253Y/Q258E/S266P, V89T/E91Q/Q225Y/Q253Y/Q258E,
V89T/Q225Y/Q253Y/Q258E/S266P,
V89T/E91Q/Q253Y/Q258E/S266P,
V89T/E91Q/Q225Y/Q258E/S266P,
E91Q/Q225Y/Q253Y/Q258E/S266P,
V89T/E91Q/Q225Y/Q253Y/Q258E/S266P,
S266P,
V89T/S266P,
E91Q/S266P,
Q225Y/S266P,
Q253Y/S266P,
V89T/E91Q/S266P,
V89T/Q225Y/S266P,
V89T/Q253Y/S266P,
E91Q/Q225Y/S266P,
E91Q/Q253Y/S266P,
Q225Y/Q253Y/S266P,
V89T/E91Q/Q225Y/S266P,
V89T/E91Q/Q253Y/S266P,
V89T/Q225Y/Q253Y/S266P,
V89T/E91Q/Q225Y/Q253Y/S266P,
V89T/E91Q,
V89T/Q253Y,
E91Q/Q253Y,
V89T/E91Q/Q253Y,
V89T/E91Q/Q225Y,
V89T/Q225Y/Q253Y,
E91Q/Q225Y/Q253Y,
V89T/E91Q/Q225Y/Q253Y,
V89T/E91Q/A202P/Q253Y,
V89T/E91Q/L213F/Q253Y,
V89T/E91Q/L213W/Q253Y,
V89T/E91Q/W243V/Q253Y,
V89T/E91Q/W243L/Q253Y,
D69F/V89T/E91Q/Q253Y,
D69Q/V89T/E91Q/Q253Y,
V89T/E91Q/T111P/Q253Y,
V89T/E91Q/T238R/Q253Y,
A36P/V89T/E91Q/Q253Y,
V89T/E91Q/A202P/L213F/Q253Y,
V89T/E91Q/A202P/L213W/Q253Y,
V89T/E91Q/A202P/W243V/Q253Y,
V89T/E91Q/A202P/W243L/Q253Y,
V89T/E91Q/L213F/W243V/Q253Y,
V89T/E91Q/L213W/W243L/Q253Y,
V89T/E91Q/L213F/W243L/Q253Y,
V89T/E91Q/L213W/W243V/Q253Y,
V89T/E91Q/A202P/L213F/W243V/Q253Y,
V89T/E91Q/A202P/L213W/W243L/Q253Y,
V89T/E91Q/A202P/L213F/W243L/Q253Y,
V89T/E91Q/A202P/L213W/W243V/Q253Y,
V89T/E91Q/A202P/Q225Y/Q253Y,
V89T/E91Q/L213F/Q225Y/Q253Y,
V89T/E91Q/L213W/Q225Y/Q253Y,
V89T/E91Q/W243V/Q225Y/Q253Y,
V89T/E91Q/W243L/Q225Y/Q253Y,
D69F/V89T/E91Q/Q225Y/Q253Y,
D69Q/V89T/E91Q/Q225Y/Q253Y,
V89T/E91Q/T111P/Q225Y/Q253Y,
V89T/E91Q/T238R/Q225Y/Q253Y,
A36P/V89T/E91Q/Q225Y/Q253Y,
V89T/E91Q/A202P/Q225Y/Q253Y/Q258E/S266P,
V89T/E91Q/L213F/Q225Y/Q253Y/Q258E/S266P,
V89T/E91Q/L213W/Q225Y/Q253Y/Q258E/S266P,
V89T/E91Q/W243V/Q225Y/Q253Y/Q258E/S266P,
V89T/E91Q/W243L/Q225Y/Q253Y/Q258E/S266P,
D69F/V89T/E91Q/Q225Y/Q253Y/Q258E/S266P,
D69Q/V89T/E91Q/Q225Y/Q253Y/Q258E/S266P,
V89T/E91Q/T111P/Q225Y/Q253Y/Q258E/S266P,
V89T/E91Q/T238R/Q225Y/Q253Y/Q258E/S266P,
A36P/V89T/E91Q/Q225Y/Q253Y/Q258E/S266P,
V89T/E91Q/A202P/L213F/Q225Y/Q253Y/Q258E/S266P,
V89T/E91Q/A202P/L213W/Q225Y/Q253Y/Q258E/S266P,
V89T/E91Q/A202P/Q225Y/W243V/Q253Y/Q258E/S266P,
V89T/E91Q/A202P/Q225Y/W243L/Q253Y/Q258E/S266P,
V89T/E91Q/L213F/Q225Y/W243V/Q253Y/Q258E/S266P,
V89T/E91Q/L213W/Q225Y/W243L/Q253Y/Q258E/S266P,
V89T/E91Q/L213F/Q225Y/W243L/Q253Y/Q258E/S266P,
V89T/E91Q/L213W/Q225Y/W243V/Q253Y/Q258E/S266P,
V89T/E91Q/A202P/L213F/Q225Y/W243V/Q253Y/Q258E/S266P,
V89T/E91Q/A202P/L213W/Q225Y/W243L/Q253Y/Q258E/S266P,
V89T/E91Q/A202P/L213F/Q225Y/W243L/Q253Y/Q258E/S266P,
V89T/E91Q/A202P/L213W/Q225Y/W243V/Q253Y/Q258E/S266P,
A202P,
L213F,
L213W,
W243V,
W243L,
D69Q,
D69F,
T111P,
T238R,
A36P,
A202P/L213F,
A202P/L213W,
A202P/W243L,
A202P/W243V,
A202P/L213F/W243L,
A202P/L213F/W243V,
A202P/L213W/W243V, and
A202P/L213W/W243L.

2. The mutant of claim 1, wherein the mutant comprises an amino acid sequence having at least 91%, 92%, 93%, 94%, 95%, 96%, 97%, 98%, or at least 99% identity with SEQ ID NO: 1.

3. The mutant of claim 1, wherein the mutant comprises an amino acid sequence having at least 99.1%, 99.2%, 99.3%, 99.4%, 99.5%, 99.6%, 99.7%, 99.8%, or at least 99.9% identity with SEQ ID NO: 1.

4. The mutant of claim 1, wherein the mutant further comprises at least an amino acid substitution selected from the group consisting of A25F, D35Y, W46E, Q62W, G70E, A73P, K75C, S80P, T114H, N126D, N137V, D142R, S146E, R159Y, T161P, N176P, K180N, S187P, V211W, Q253V, Y255D, T327Y, and A380P.

5. The mutant of claim 4, wherein the at least one amino acid substitution is a combination selected from the group consisting of:
W46E/Q62W/G70E/A73P/K75C/T114H/N137V/D142R/S146E/R159Y/Y255D,
A25F/W46E/Q62W/G70E/A73P/K75C/T114H/N137V/D142R/S146E/R159Y/Y255D, W46E/Q62W/G70E/A73P/K75C/T114H/N137V/
D142R/S146E/R159Y/Y255D/A380P,
A25F/W46E/Q62W/G70E/A73P/K75C/T114H/N137V/
D142R/S146E/R159Y/Y255D/A380P,
W46E/Q62W/G70E/A73P/K75C/S80P/T114H/N137V/
D142R/S146E/R159Y/N176P/S187 P/Y255D/A380P,
A25F/W46E/Q62W/G70E/A73P/K75C/S80P/T114H/
N137V/D142R/S146E/R159Y/N176P/S187P/Y255D/
A380P,
W46E/Q62W/G70E/A73P/K75C/S80P/T114H/N137V/
D142R/S146E/R159Y/T161P/ N176P/S187P/Y255D/
A380P, and
A25F/W46E/Q62W/G70E/A73P/K75C/S80P/T114H/
N137V/D142R/S146E/R159Y/T161P/N176P/S187P/
Y255D/A380P.

6. A DNA molecule encoding the phytase mutants of claim 1.

7. A vector comprising the DNA molecule of claim 6.

8. A host cell, wherein the host cell comprises the vector of claim 7.

* * * * *